United States Patent [19]

Heifetz

[11] Patent Number: 5,571,121
[45] Date of Patent: Nov. 5, 1996

[54] ATRAUMATIC CLAMP FOR TEMPORARY OCCLUSION OF BLOOD VESSELS

[76] Inventor: Milton D. Heifetz, 704 N. Bedford Dr., Beverly Hills, Calif. 90210

[21] Appl. No.: 410,870

[22] Filed: Mar. 28, 1995

[51] Int. Cl.⁶ .................................................. A61B 17/00
[52] U.S. Cl. ........................ 606/158; 606/151; 606/205; 606/207
[58] Field of Search .................................. 606/151, 157, 606/158, 219, 221, 139, 205, 207, 208, 210, 211; 227/902

[56] References Cited

U.S. PATENT DOCUMENTS

| | | | |
|---|---|---|---|
| 3,279,479 | 10/1966 | Solomon | 606/157 |
| 3,867,944 | 2/1975 | Samuels | 606/158 |
| 4,957,500 | 9/1990 | Liang et al. | 606/157 |
| 5,062,846 | 11/1991 | Oh et al. | 606/158 |

*Primary Examiner*—Michael Powell Buiz
*Assistant Examiner*—Jeffrey A. Schmidt
*Attorney, Agent, or Firm*—Donald D. Mon

[57] ABSTRACT

An atraumatic occluder for the temporary occlusion of tubular vessels in the human body. The occluder includes a first jaw and a second jaw, each of which have a pressure face. A mounting member joins the jaws so that the pressure faces are opposed to one another. Spacer members are located on at least one of the pressure faces and rise to a known height above the pressure face so as to contact the other pressure face when the jaws are brought together. The height of the spacer members is approximately equal to twice the wall thickness of a vessel to be clamped so that the vessel is compressed and its lumen closed to flow when the spacer members make contact with the pressure face. A plurality of spacer members are spaced from one another along the pressure faces so as to prevent a vessel held therebetween from slipping from the jaws. The spacer members are spaced from one another at least and approximately the width of the vessel to be clamped.

8 Claims, 1 Drawing Sheet

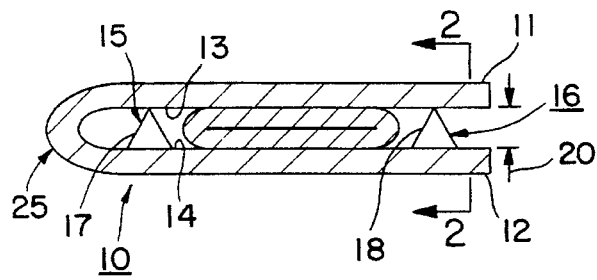
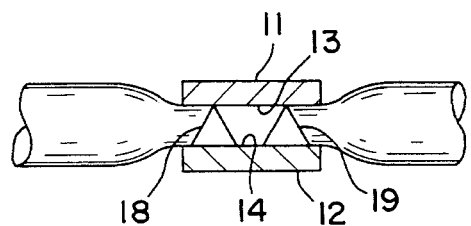
FIG. 1  FIG. 2
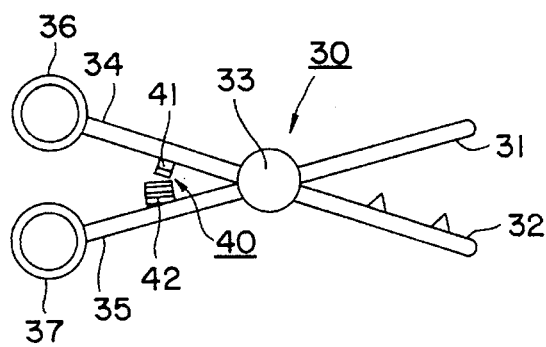
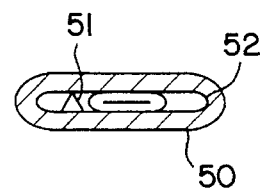
FIG. 3  FIG. 4
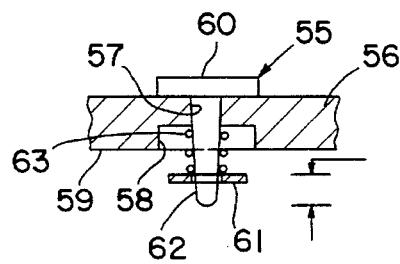
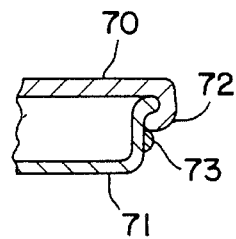
FIG. 5  FIG. 6

ATRAUMATIC CLAMP FOR TEMPORARY OCCLUSION OF BLOOD VESSELS

FIELD OF THE INVENTION

Occluders such as clips and clamps temporarily to close flexible vessels within the body such as a vein or an artery, with minimal trauma.

BACKGROUND OF THE INVENTION

Vessels such as veins and arteries are closed during surgery by clamps and clips as exemplified by surgical hemestats intracranial aneurism clips. Such devices press against opposite sides of a flexible hollow tube so that the walls flatten out and bear against one another. This produces an axially-extending fold at the two edges.

For stopping the flow of fluid through the vessel, this squeezing or pinching action is very effective. However, the lumens of these vessels have linings (intima) which should not be traumatized by strong distortions. Strong pressures, and excessive bending (axial folding), can traumatize them which can lead to complications after the occluder is removed, and flow through the vessels in restored.

The compressive force of conventional clamps and clips relies on the strength of a spring mechanism as exemplified by intracranial aneurism clips with softened spring action, which are used for temporary occlusion of blood vessels, or on the surgeon's sense of feel that the vessel has been closed when using a hemostat-like clamp. This is a highly subjective decision, heavily reliant on the surgeon's experience and dexterity. It requires that he pay very close attention so that the vessel and its lining are not crushed or otherwise traumatized.

Another disadvantage of conventional clamps is in their locking means. Ratchets are used which will lock incrementally but they are so designed that a closure of the jaws which is just right might require a further compression so the instrument can reach a locking position, thereby causing trauma to the inner wall of the vessel.

It is an object of this invention to provide occluders which will, without requiring immediate judgement by the surgeon, positively stop at a known amount of closure, and clamps which with further movement of manipulative means in order to latch the device will not cause an additional compression of the vessel.

Each spring-based occluder will have one active setting designed to flatten together and approximate the walls of the vessel so that flow of fluid (blood) will be stopped. Degree of closure of the occluders will be tailored to specific vessels depending upon their diameter and wall thickness. There is a surprising uniformity among various sets of vessels. A surgeon can quickly judge which size occluder he will use, and can set it quickly and without concern that he will over-compress the vessel.

For a hemostat type of vessel occluder, the design prevents excessive pressure on the vessel but still will permit the surgeon to vary the compressive force of the instrument blades within certain inherent limits.

It is an object of this invention to provide occluders which provide the above-described advantages.

BRIEF DESCRIPTION OF THE INVENTION

Occluders according to this invention include a pair of jaws joined together by mounting means. Each jaw has a pressure face. The mounting means enables the jaws to be brought toward one another with a vessel between them, so that the pressure faces engage the vessel, and as they approach one another the vessel is compressed until finally it is closed to flow. A hemostat is an example of the clamp principle. An intracranial aneurism clip is an example of the clip principle.

With this invention, there will always remain a predetermined spacing between the pressure faces which will prevent a crushing effect upon a vessel of respective dimensions but which enables the vessel to be compressed sufficiently to prevent flow of fluid through it.

In the clip embodiment of the invention, the mounting means is a flexible spring, made self with the jaws. The stop means comprises at least two spacers on the jaws so disposed and arranged as to limit the approach of one pressure face to the other. The space between the pressure faces when the clip is closed will be narrow enough to approximate the walls of the vessel, i.e. about twice the wall thickness of the vessel, and wide enough to prevent crushing the walls of the vessel. Two projections are necessary for separating the blades in the clip so that there will be no slippage of the vessel in either direction along the axis of the clip. They are spaced apart by about the width of the compressed vessel.

In the clamp approach, according to yet another embodiment of the invention, the mounting means is a hinge, and scissor levers are connected to respective jaws so that when they are brought toward one another, the pressure faces are brought toward one another.

According to yet another preferred but optional feature of the invention, latch means is provided to hold the clamp jaws in their set condition.

The above and other features of this invention will be fully understood from the following detailed description and the accompanying drawing, in which:

BRIEF DESCRIPTION OF THE DRAWINGS

FIG. 1 is a longitudinal cross-section of the presently preferred embodiment of the invention;

FIG. 2 is a cross-section taken at line 2–2 in FIG. 1;

FIG. 3 is a side view of another embodiment of the invention;

FIG. 4 is a fragmentary cross-section of a modification of the clip of FIG. 1;

FIG. 5 is a fragmentary cross-section showing another embodiment of a spacer; and FIG. 6 is a fragmentary cross-section showing another embodiment of latch means.

DETAILED DESCRIPTION OF THE INVENTION

The object of this invention is to provide a strong enough compression on a vessel to overcome the hydrodynamic, peristaltic, and other forces on the vessel so as to stop the flow of fluid through it, but not enough to damage the vessel, and especially not so strong as to traumatize its intima. An occluder 10 for this purpose is shown in FIG. 1. This embodiment of occluder is a clip which is inherently biased closed.

Clip 10 includes jaws 11, 12 which have respective pressure faces 13, 14. When the clip is closed, it is best design for these faces to be parallel to one another. Face 14 includes two sets of spacers, set 15 and set 16. In this embodiment there will be four of such spacers, of which only spacers 17, 18 and 19 are shown. They rise to a nominal height 20 above face 14.

It will be recognized that the spacers could be placed instead on the other face, or that they could be divided between the two faces. Also, instead of post-like shapes they could instead be ridge-like. The objective is to define a known minimum spacing 20 between the pressure faces when the clip is closed on a vessel. The jaws will be opened by a holder while they are being applied. The jaws are joined together by mount means 25, in this embodiment a flexible resilient bight. At least two of the spacers are spaced apart along the axis of the pressure face to prevent the vessel from slipping away these vessels generally being quite slippery.

The mount means is made of a springy resilient metal which when formed tends to hold the jaws in the closed position shown in FIG. 1. The clip will be opened with a suitable tool. This embodiment does not require a latch means, because it is inherently self-latching.

FIG. 3 is a scissors-like clamp 30 with jaws 31, 32 identical to jaws 11, 12. In this embodiment the mount means is a hinge 33 which pivotally mounts the jaws. Handles 34, 35 are respectively connected to jaws 31, 32, and include finger loops 36, 37. Latch means 40 in the form of a tooth 41 on handle 34, and a group of ratchet grooves 42 on handle 34 will engage reliably to hold the handles in an adjusted position, and thereby hold the jaws in an adjusted position.

One or both of the handles, or of the jaws, may be made sufficiently springy that when the jaws are closed against the spacers, the ratchet can overtravel to its next setting.

FIG. 4 illustrates a modification of the spacer means where one jaw 50 bears one or mope spacers 51, and the other bears a ledge 52 positioned to bear against the opposite jaw.

FIG. 5 illustrates a spacer 55 which can give the surgeon some feel for the closure. Jaw 56 has a passage 57 with a counterbore 58 in pressure face 59. A headed pin 60 fits in the passage and carries a collar 61 fitted in groove 62. A spring 63 is placed in the counterbore around the shank of the pin. When the opposite jaw presses the tip toward the counterbore, the spring and collar move into the counterbore. The tip projects the correct distance from the pressure face. The advantage of this construction is that the surgeon can feel the effects of the closure as the jaws gradually approach full contact. He is given guidance whether he has selected a correct size.

FIG. 6 is a fragmentary showing of jaws 70, 71 with latch means on the jaws themselves. An overhanging tooth 72 is adapted to snap into latch grooves 73 on jaw 71. As in the embodiment of FIG. 3, the tooth can overtravel to make a positive latch, but will not excessively compress the vessel.

Occasionally there may be some situations where compression beyond initial contact of the spacers may be desired. For example, as in FIG. 5, an initial contact which can be felt, or which might be sufficient is desired, but if the surgeon sees that flow continues through the vessel, he may exert further compression, and the spacer itself might yield a bit such as by compressive deformation. This will be permitted only to a limited extent. There will always be a minimum spacing that is guaranteed to exist. A semi-rigid silicone spacer can be designed for this purpose.

In summary, the spacing should be not less than twice the wall thickness of the vessel so as not to damage the vessel. It nay and often will be a bit greater than that, because the viscosity of the fluids is such that flow through an extremely narrow slit is unlikely. The objective in any event is to avoid crushing the wall of the vessel.

This device is designed for temporary occlusion of vessels which are not to be cut immediately adjoining the instrument.

This invention is not to be limited by the embodiments shown in the drawings and described in the description, which are given by way of example and not of limitation, but only in accordance with the scope of the appended claims.

I claim:

1. An atraumatic occluder for the temporary occlusion of tubular vessels in the human body, said vessels comprising a cylindrical wall having a dimension of wall thickness and a lumen lined by an intima layer whose disruption is to be minimized when the vessel is compressed to close the lumen to flow, said occluder comprising:

a first jaw and a second jaw, each said jaw having a pressure face, said pressure faces being opposed to one another;

mount means joining said jaws so the pressure faces can be moved toward and away from one another; and spacer means on at least one of said pressure faces rising to a known height above said pressure face, and facing said other pressure face so as to be contacted by said other pressure face to prevent further movement of said pressure faces toward one another, said height being approximately equal to twice said wall thickness so that the vessel is compressed and its lumen closed to flow when the spacer means make said contact, a plurality of said spacers means being spaced apart from one another along said pressure faces so as to prevent a vessel held between them from slipping from between the jaws, said spacing apart of the spacer means being at least, and approximately the width of the compressed vessel.

2. An occluder according to claim 1 in which said occluder is a clip, and in which said mount means includes springy means to bias said jaws toward one another.

3. An occluder according to claim 2 in which said springy means is inherent in a springy bight which is integral with said jaws.

4. An occluder according to claim 1 in which said spacer is deformable to a limited extent to allow for limited approach of said jaws toward one another after initial contact of the spacer means with an opposite jaw.

5. An occluder according to claim 1 in which said spacer means comprises a headed pin fitted in a passage through a jaw, including a shank which protects beyond its respective pressure face, and bias means biasing said shank beyond said pressure face to form a spacer with limited axial movement.

6. An occluder according to claim 1 in which said mount means pivotally joins said jaws, a handle portion connected to each said jaw, and ratchet means between said handles to hold the handles and the jaws in an adjusted position.

7. An occluder according to claim 6 in which at least one of said handles include a springy portion which permits slight overtravel of the ratchet means in order to latch at a jaw spacing established by the spacers.

8. An occluder according to claim 1 in which latch means is provided on said jaws to hold them in a position established by the spacer means.

* * * * *